(12) United States Patent
Becker et al.

(10) Patent No.: US 10,983,124 B2
(45) Date of Patent: Apr. 20, 2021

(54) DEVICE FOR DETECTING LEUKOCYTES IN AN AQUEOUS FLUSHING SOLUTION

(71) Applicants: Franz Ferdinand Becker, Rodgau (DE); Ulrich Paul Hinkel, Weimar (DE)

(72) Inventors: Franz Ferdinand Becker, Rodgau (DE); Ulrich Paul Hinkel, Weimar (DE)

(*) Notice: Subject to any disclaimer, the term of this patent is extended or adjusted under 35 U.S.C. 154(b) by 145 days.

(21) Appl. No.: 15/713,883

(22) Filed: Sep. 25, 2017

(65) Prior Publication Data

US 2019/0094222 A1  Mar. 28, 2019

(51) Int. Cl.
| | | |
|---|---|---|
| *G01N 33/569* | (2006.01) | |
| *G01N 21/82* | (2006.01) | |
| *G01N 21/53* | (2006.01) | |
| *G01N 33/49* | (2006.01) | |
| *G01N 21/85* | (2006.01) | |

(52) U.S. Cl.
CPC ..... *G01N 33/56972* (2013.01); *G01N 21/534* (2013.01); *G01N 21/82* (2013.01); *G01N 21/85* (2013.01); *G01N 33/49* (2013.01)

(58) Field of Classification Search
CPC ........... G01N 33/56972; G01N 21/534; G01N 21/82
See application file for complete search history.

(56) References Cited

U.S. PATENT DOCUMENTS

| | | | | |
|---|---|---|---|---|
| 2,835,252 A | | 5/1958 | Mauchel | |
| 4,685,464 A | * | 8/1987 | Goldberger | A61B 5/14552 600/344 |
| 5,247,931 A | * | 9/1993 | Norwood | A61B 5/02427 24/490 |
| 5,343,869 A | * | 9/1994 | Pross | A61B 5/02055 600/301 |
| 5,490,523 A | * | 2/1996 | Isaacson | A61B 5/02427 600/323 |
| 2008/0081967 A1 | * | 4/2008 | Andersohn | A61B 5/061 600/310 |
| 2008/0098798 A1 | * | 5/2008 | Riley | A61M 5/365 73/19.03 |
| 2009/0078047 A1 | | 3/2009 | Dam | |
| 2009/0149776 A1 | | 6/2009 | Adams | |
| 2017/0136166 A1 | | 5/2017 | Chen et al. | |

FOREIGN PATENT DOCUMENTS

| | | |
|---|---|---|
| EP | 0491971 A1 | 7/1992 |
| JP | 3549262 B2 | 8/2004 |
| JP | H 0898882 * | 8/2004 |

* cited by examiner

*Primary Examiner* — Brian R Gordon
*Assistant Examiner* — Dwan A Gerido
(74) *Attorney, Agent, or Firm* — Greer, Burns & Crain, Ltd.

(57) ABSTRACT

The device for detecting turbidity in an aqueous flushing solution is characterized by a base body, at least one light source, a detector device at which the at least one light source is aimed, a holding unit for a component, containing the flushing solution, between the at least one light source and the detector device, and a display device for the findings of turbidity detected.

6 Claims, 2 Drawing Sheets

DEVICE FOR DETECTING LEUKOCYTES IN AN AQUEOUS FLUSHING SOLUTION

FIELD OF THE INVENTION

The invention relates to an apparatus that detects turbidity caused by leukocytes and/or luminescence in the PD (peritoneal dialysis) bag or in the tubing in liquids after their medical use.

SUMMARY OF THE INVENTION

The invention relates to an apparatus that detects turbidity caused by leukocytes and/or luminescence in the PD (peritoneal dialysis) bag or in the tubing in liquids after their medical use. The turbidity due to leukocytes or the luminescence thereof may be caused by bacteria, cells, or other particles. The liquids are preferably liquids for use in all PD solutions used in the various peritoneal dialysis methods or flushing solutions that are used in the flushing of organs and the peritoneum. The invention is not limited to detecting and measuring the turbidities and leukocytes of the flushing solutions listed in the foregoing, but instead may be used very generally for a wide variety of liquids.

In addition, the device or apparatus may also indicate other changed properties of the liquid that are caused by bacteria, cells, or particles.

For quite some time there has been a need for a device that can determine, preferably in an on-line method, changes in the property in liquids after the liquids have been used, preferably for a medical application or even a non-medical application.

This object is inventively attained by a device for detecting leukocytes in an aqueous flushing solution that comprises a base body, at least one light source, a detector device at which the at least one light source is aimed, a holding unit for a component, containing the flushing solution, between the at least one light source and the detector device, and a display device for the findings of the leukocyte measurement.

Advantageous embodiments of the invention are described herein below.

The inventive device includes a base body, at least one light source, a detector device at which the at least one light source is aimed, a holding unit for a component, containing the flushing solution, between the at least one light source and the detector device, and an evaluation and display device for the findings of the leukocyte measurement. A transparent component containing the liquid or conducting the flowing liquid is irradiated in the device or apparatus, and the quantity of light not absorbed or the quantity of light occurring due to luminescence is detected using the detector device. The detected quantity of light provides information about the detected leukocytes or luminescence of the liquid. The quantity of light detected is analyzed by an evaluation device, and the measured values thus obtained are displayed, preferably visually, using an evaluation device. The measured values obtained may also be displayed acoustically or using vibration.

To this end, the detector device may have a sensor for measuring the non-absorbed quantity of light and/or the quantity of light occurring due to luminescence. Likewise, the detector device may include a sensor that identifies and measures bacteria, cells, or particles by adding an indicator to the liquid. These impurities may also be identified and measured, using a suitable sensor, by the coloration of the liquid. The changes in the liquid may also be detected with a microscope. Another option is for the detector device to have sensors that detect or measure a changed electrical conductivity, a changed viscosity, density or interfacial tension of the liquid, etc.

The device may also be provided with an acoustic signal generator to provide an indication of the measured leukocytes or their luminescence. It is also possible to determine a specific degree of change in the properties of the liquids that should act as a warning if it is attained.

The device may be employed in in-patient, out-patient, and skilled nursing situations. It may also be used independently by a patient in home care.

In one preferred embodiment, the base body of the device has the shape of a clamp that comprises two clamp parts that are connected to one another in an articulated manner and are caused to move into a closed position by a spring. The two clamp parts preferably have two opposing recesses in which a transparent tubing, cannula, or another container for the flushing solution may be fixed. If tubing is used, a liquid flowing therethrough may be measured, while in the case of a securely clamped cannula standing liquid is measured.

The holding unit for the container of flushing solution may also comprise only one recess in one clamp part, while the other clamp part clamps the container such that it is fixed in the clamp.

In another embodiment it is provided that the at least one light source and a housing with a current connection are attached to one clamp part and the detector device and the evaluation and display device are attached to the other clamp part. A clamp may be attached to one clamp part such that the entire device may be securely clamped, e.g., to an infusion rod.

In another embodiment of the device, the base body is a stand housing, preferably standing on feet, having a recess in the top into which a transparent container for the flushing solution may be placed, wherein the at least one light source and the detector device are arranged opposing one another on the edge of the recess such that the light passes through the lower region of the container for the flushing solution.

The container may be a rigid funnel into which a flexible bag, also transparent, having the flushing solution may be placed. In this case the measurement is taken on the standing liquid.

The power supply for the at least one light source, the detector device, the evaluation device, and the display device are preferably housed in the stand housing.

A laser is preferably used for the laser source, wherein a plurality of lasers may also be used.

Additional details of the invention may be taken from the attached drawings and the description for them. Schematically depicted are:

DETAILED DESCRIPTION OF PREFERRED EMBODIMENTS

Figures 1A, 1B:
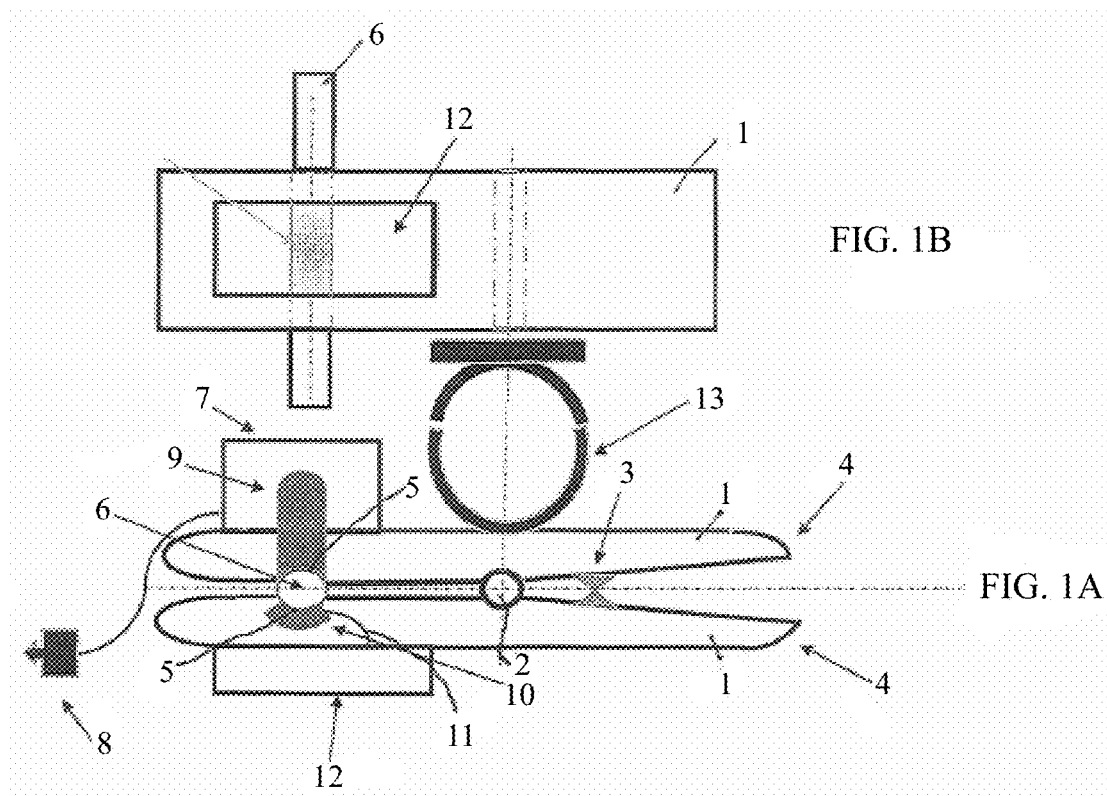
FIGS. 1A and 1B: a side view and a top view of first embodiment of the inventive device.

FIGS. 1A and 1B depict one embodiment as a type of clamp system. The base body of the device has the shape of a clamp that constitutes two clamp parts 1. The clamp parts 1 are connected to one another by an articulation 2 approximately in the center of their longitudinal extension. A spring 3 arranged between the clamp parts 1 presses the ends of the two clamp parts 1 away from one another into the closed position of the clamp. The clamp may be opened in that the user exerts pressure with his fingers onto the ends 4 of the two clamp parts 1. Opposing recesses 5, in which a tubing 6 may be fixed, through which tubing the liquid to be examined flows, are embodied in the front region of the clamp in the two clamp parts 1. It is also possible to retain, e.g., a cannula having a standing liquid in the clamp in the same manner.

Attached to the top clamp part 1 in FIG. 1A is a housing 7 in which is arranged a power connection that is supplied with current by an external charging device 8 with a power supply voltage or by a battery. Also arranged in the housing 7 is a light source 9, the light from which travels through a channel in the top clamp part 1 to the tubing 6. Housed in the other clamp part on the opposing side is a detector 10 that is provided with an evaluation device and is connected via a line 11 to a display field 12 that is attached to the exterior of the bottom clamp 1 in the figure.

A clamp 13, to which the entire device may be attached, e.g., for an infusion rod, is attached to the top clamp part 1.

FIG. 1B is a side view of the clamp part 1 with the display field 12 and a tubular container 6 for the liquid to be examined.

Figure 2A:
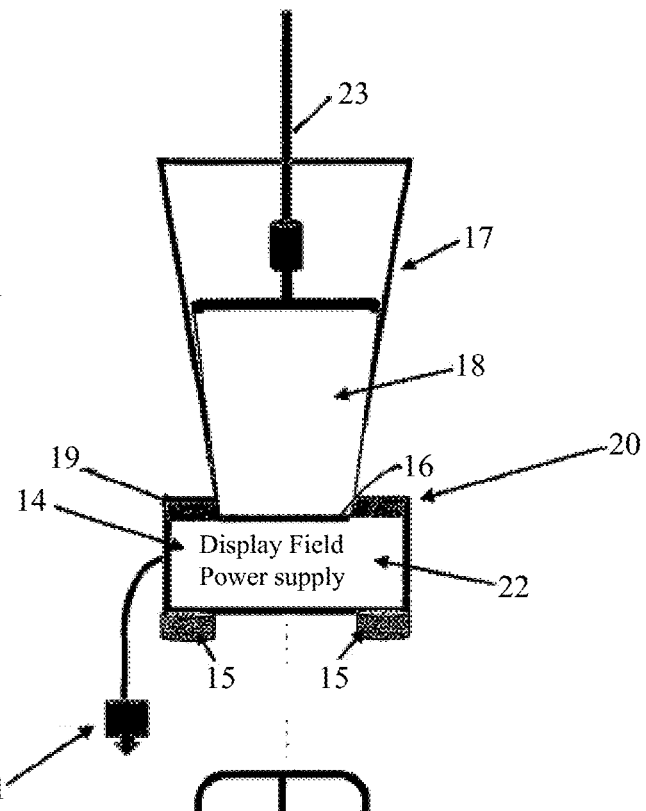
FIGS. 2A and 2B: another embodiment, also shown in a side view and a top view.
Figure 2B:
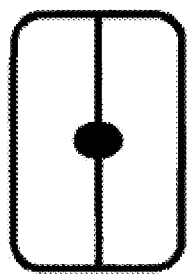

FIGS. 2A and 2B depict a different embodiment of the invention. A stand housing 14 that rests on feet 15 has a recess 16 in its top. A rigid funnel 17 that can accommodate a flexible bag 18 is placed into this recess 16. This flexible bag is filled with the used flushing solution via a line. The flexible bag may also be placed into the funnel 17 for the measurement after it has been filled. A light source 19 and a detector device 20 are arranged opposing one another on either side of the recess 16 in the stand housing. The emitted light travels through the lower region of the funnel 17 and flexible bag that contains the liquid.

Also housed in the stand housing 14 is the power supply for the light source 19, the detector device 20, and an evaluation device for the resulting figures. The power is supplied using the battery or network power supply 21. A display field 22 for the results found is attached to an exterior side of the stand housing 14.

The top of the flexible bag 18 is provided with a flexible tubing 23 via which the flexible bag 18 is filled with the used flushing solution and may be removed from the funnel 17.

The invention claimed is:

1. A device for detecting leukocytes and other turbidities in aqueous flushing solutions after their medical or non-medical use, comprising a base body, at least one light source, a detector device at which the at least one light source is aimed, a holding unit for a component containing the flushing solution, between the at least one light source and the detector device, and a display device for the findings of the leukocyte measurement,
    wherein the base body has the shape of a clamp that comprises two elongated clamp parts each having a longitudinal axis, wherein the clamp parts are connected to one another in an articulated manner at a single pivot point, and are caused to move into a closed position by a spring, wherein the spring is oriented perpendicular to the longitudinal axis of each of the two clamp parts and extends between the two clamp parts, and in that the holding unit has two opposing recesses in the clamp parts, wherein the two opposing recesses are concave and oriented around an axis that is perpendicular to the longitudinal axis of each of the two clamp parts in which the two opposing recesses are configured to receive a transparent tubing for the flushing solution, and
    wherein the at least one light source and a housing with a power connection are attached to one clamp part and the detector device and the display device are attached to the other clamp part.

2. The device according to claim 1, wherein a clamp with which the device may be securely clamped to an infusion rod is attached to one clamp part.

3. The device according to claim 1, wherein the detector device has a sensor for measuring the non-absorbed quantity of light, and/or the quantity of light resulting from luminescence, and/or a sensor for measuring electrical conductivity, and/or a sensor for measuring the viscosity, density, and interfacial tension.

4. The device according to claim 1, wherein one or a plurality of lasers is/are used for the light source.

5. The device according to claim 1, wherein the two opposing recesses are generally concave in cross-section as viewed along the longitudinal axis of the clamp parts such that the two opposing recesses are configured to receive the transparent tubing or the cannula for the flushing solution.

6. The device according to claim 1, wherein the single pivot point is fixed.

\* \* \* \* \*